United States Patent
Jones et al.

(10) Patent No.: US 7,231,819 B2
(45) Date of Patent: Jun. 19, 2007

(54) CHEMICAL SENSOR FOR WELLBORE APPLICATIONS

(75) Inventors: Timothy Gareth John Jones, Cottenham (GB); Li Jiang, Cambridge (GB); Andreas Manz, East Molesey (GB); Ratna Tantra, London (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 7 days.

(21) Appl. No.: 10/297,773

(22) PCT Filed: Jun. 11, 2001

(86) PCT No.: PCT/GB01/02546

§ 371 (c)(1),
(2), (4) Date: Sep. 12, 2003

(87) PCT Pub. No.: WO01/98630

PCT Pub. Date: Dec. 27, 2001

(65) Prior Publication Data

US 2004/0045350 A1    Mar. 11, 2004

(30) Foreign Application Priority Data

Aug. 21, 2000 (GB) ................... 0015052.4

(51) Int. Cl.
  *E21B 49/00*    (2006.01)
  *G01N 30/84*    (2006.01)
(52) U.S. Cl. ................... 73/152.23; 73/61.55
(58) Field of Classification Search ............ 73/152.23, 73/152.24, 152.25, 61.52, 61.53, 61.54, 61.55, 73/61.59, 61.61, 152.04, 152.02, 152.18, 73/863.81, 61.58; 210/198.2, 198.3
See application file for complete search history.

(56) References Cited

U.S. PATENT DOCUMENTS

| 3,530,711 | A | * | 9/1970 | Tocanne | 73/152.23 |
| 4,006,630 | A | * | 2/1977 | Cathriner | 73/152.53 |
| 4,577,492 | A | * | 3/1986 | Holba et al. | 73/61.53 |
| 4,661,459 | A | | 4/1987 | Hirtz | |
| 4,676,310 | A | * | 6/1987 | Scherbatskoy et al. | 340/853.4 |
| 4,739,654 | A | | 4/1988 | Pilkington et al. | |
| 4,904,603 | A | * | 2/1990 | Jones et al. | 436/25 |
| 5,042,297 | A | * | 8/1991 | Lessi | 73/152.31 |
| 5,095,983 | A | * | 3/1992 | Magnani | 166/250.01 |
| 5,147,561 | A | | 9/1992 | Burge et al. | |

(Continued)

FOREIGN PATENT DOCUMENTS

GB    2 216 569 A    10/1989

OTHER PUBLICATIONS

Definition of "organic" from Merriam-Webster OnLine dictionary, 2 pages.*

(Continued)

*Primary Examiner*—Hezron Williams
*Assistant Examiner*—John Fitzgerald
(74) *Attorney, Agent, or Firm*—Steven Gahlings; Jody Lynn DeStefanis; Dale Gaudier

(57) ABSTRACT

There is described an analyzing device having two separation units to separate molecular species to detect molecular species in wellbore fluids with both separation units operating under forced flow conditions to provide for an active separation of subterranean wellbore effluent into its components for subsequent analysis.

17 Claims, 9 Drawing Sheets

U.S. PATENT DOCUMENTS

| | | | |
|---|---|---|---|
| 5,329,811 A * | 7/1994 | Schultz et al. | 73/152.02 |
| 5,338,448 A * | 8/1994 | Gjerde | 210/198.2 |
| 5,361,632 A * | 11/1994 | Magnani | 73/152.14 |
| 5,616,407 A * | 4/1997 | Fritz et al. | 442/118 |
| 5,673,752 A | 10/1997 | Scudder et al. | |
| 5,837,893 A * | 11/1998 | Chu | 73/152.52 |
| 5,859,430 A * | 1/1999 | Mullins et al. | 250/255 |
| 6,033,546 A | 3/2000 | Ramsey | |
| 6,223,822 B1 * | 5/2001 | Jones | 166/250.05 |
| 6,305,216 B1 * | 10/2001 | Samaroo | 73/53.01 |
| 6,938,470 B2 * | 9/2005 | DiFoggio et al. | 73/152.24 |
| 6,939,717 B2 * | 9/2005 | Jiang et al. | 436/121 |
| 6,964,301 B2 * | 11/2005 | Hill et al. | 166/264 |
| 7,090,012 B2 * | 8/2006 | Hill et al. | 166/264 |
| 2004/0000193 A1 * | 1/2004 | Grotendorst et al. | 73/152.23 |

OTHER PUBLICATIONS

Definition of "chromatography" from Merriam-Webster OnLine dictionary, 2 pages.*

* cited by examiner

CHEMICAL SENSOR FOR WELLBORE APPLICATIONS

The invention relates to a chemical sensor tool for use in downhole analyzing of fluids produced from subterranean formations.

BACKGROUND OF THE INVENTION

Analyzing samples representative of downhole fluids is an important aspect of determining the quality and economic value of a hydrocarbon or water producing formation.

Present day operations obtain an analysis of downhole fluids usually through wireline logging using a formation tester such as the MDT™ tool of Schlumberger Oilfield Services. However, more recently, it was suggested to analyze downhole fluids either through sensors permanently or quasi-permanently installed in a wellbore or through sensor systems mounted on a drillstring. The latter method, if successful implemented, has the advantage of obtaining data while drilling, whereas the former installation could be part of a control system for wellbores and hydrocarbon production, therefrom.

To obtain first estimates of the composition of downhole fluids, the current MDT™ tool uses an optical probe to estimate the amount of hydrocarbons in the samples collected from the formation. Other known sensors use resistivity measurements to discern various components of the formations fluid.

To meet demand for chemical measurements of increasing accuracy, it may appear obvious to adapt chemical analysis tools known from chemical laboratory practice to the hostile environment of a subterranean borehole. Such known analysis tools include for example the various types of chromatography, electrochemical and spectral analysis. However, a closer look at the environmental conditions within a subterranean wellbore lets those attempts appear as futile.

Various types of downhole measurement tools are known. Examples of such tools are found in the U.S. Pat. Nos. 6,023,340; 5,517,024; and 5,351,532 or in the International Patent Application WO 99/00575.

It is therefore an object of the present invention to provide apparatus and methods that would allow the use of chemical analysis tools known per se in a subterranean wellbore.

SUMMARY OF THE INVENTION

It was found that many problems associated with the use of sensitive chemical analysis tools are grounded on a lack of purity of samples as acquired from downhole formation.

Therefore, there is provided a wellbore fluid sampling device comprising at least two separation stages for a sample of downhole fluids characterized in that within each of said at least two separation stages components of the sample are separated by an active force.

Active forces as contemplated by the present invention may be pressure gradients as generated by pumps, or electrical fields generated by electrodes connected to different potentials, or a combination of both. Each stage may be equipped with its own force generator.

A separation stage is defined herein as a device or system that separates fluid phases or, within a fluid phases, molecules or ions according to their chemical or physical properties. Not included in the definition of a separation stage are mesh type filters. Those filters are widely used to remove solid particles from the fluid samples. In contrast, the separation stages within the context of the present invention generally assume that the fluid sample at its input have been already subjected to a solid removal process.

A separation stage in accordance with the present invention may comprise selective membranes, or chromatographic channels, i.e. paths along which different species migrate with different velocities.

The molecular target species considered by the present invention are cations such as $Ca^{2+}$, $Mg^{2+}$, $Sr^{2+}$, $Ba^{2+}$, $Na^+$ or $K^+$, anions such as $CO_3^{2-}$, $SO_4^{2-}$-$PO_4^{3-}$ or $Cl^-$, various hydrocarbons as encountered in subterranean formations, or gases such as $H_2S$, $CO_2$, $CH_4$, or $He$.

In a preferred embodiment of the invention, at least one separation unit comprises an ion-selective membrane, or, even more preferable, a potentiometric sensor with an ion-selective membrane.

The device is preferably adapted to operate as sensor for various downhole applications, including wellbore logging, measurement-while-drilling (MWD), or permanent monitoring, i.e. as a fixed installation within the borehole.

Another industrial application of the present invention is the management and control of subterranean water reservoirs and aquifers.

These and other features of the invention, preferred embodiments and variants thereof, possible applications and advantages will become appreciated and understood by those skilled in the art from the following detailed description and drawings.

DRAWINGS

FIG. 1 shows a schematic diagram of the main elements in accordance with the present invention;

FIGS. 2A, B show details of two examples in accordance with the present invention;

MODE(S) FOR CARRYING OUT THE INVENTION

Figure 1:
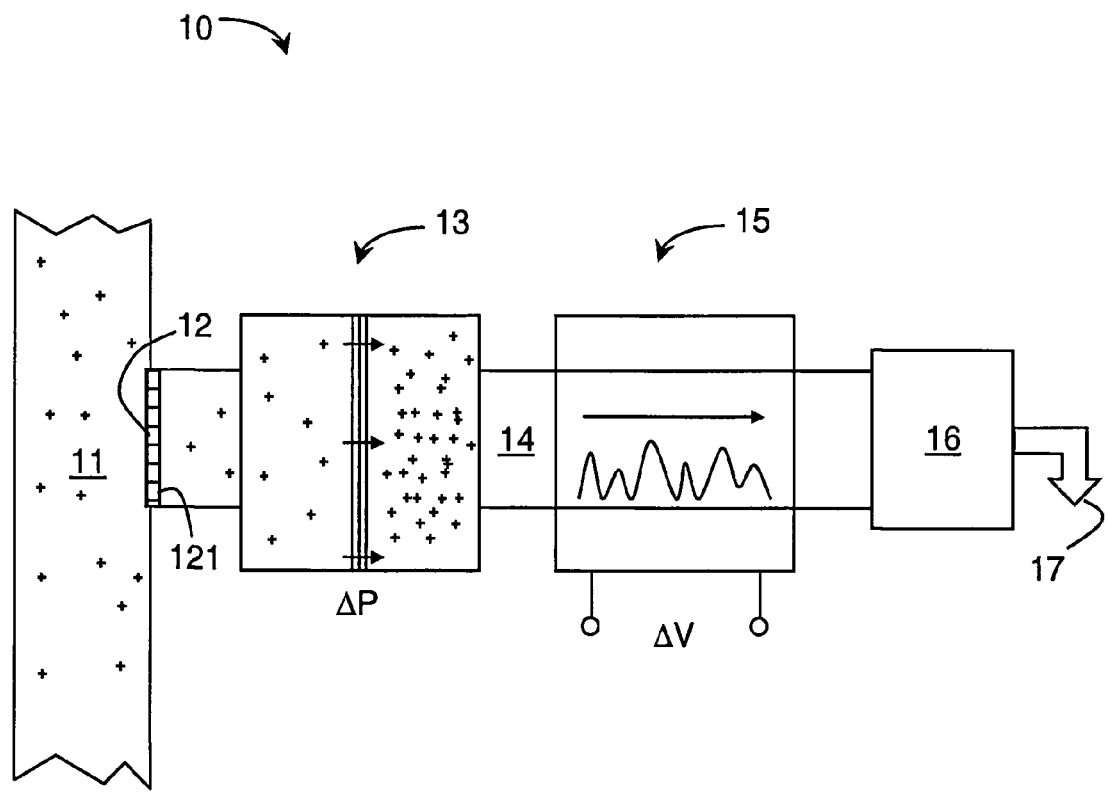

In FIG. 1, there is schematically illustrated how elements of an analyzing tool in accordance with the present invention interact to achieve a better separation of the components of a downhole fluid and, hence, more accurate testing results.

According to FIG. 1, a flow conduit 11 is provided with an opening 12 through which at least a part of a fluid flowing through the conduit can enter into a first separation unit 13. At the outlet of the first separation unit a conduit or flow channel 14 then provides a flow path to the second separation unit 15. The outlet of the second separation unit has communicates with a sensor unit 16 used to perform the detection of the separated species of the flow. An outlet 17 is provided for the disposal of the fluid that migrated through the device.

The flow conduit 11 may be communicating directly with the fluids produced from the well. Or, alternatively, the conduit can be a by-pass of a main conduit carrying at least parts of the produced fluids. The conduit 11 may contain the original fluid flow as produced from the formation or a pre-processed fluid.

Between the conduit and the separation units there is a shown a mesh 121 to prevent solid particles from entering the tool.

In the example depicted in FIG. 1, the separation units are drawn schematically as membrane type (separation unit 13) and as separation column type (separation unit 15), respectively. The selection of the precise separation mechanism is much a matter of choice and depends on the species involved and upon design considerations. The two separation mechanisms considered for this example are firstly phase selective membranes such as gas stripping membranes (surface selective flow membranes) for gaseous phases and $ZrSO_4$, PTFE or silicon rubber membranes to separate gas from an aqueous or organic phase. The second mechanism is based on the variation of the migration or diffusion pattern of a species though a medium, and is usually known as chromatography.

Both units 13, 15 have an independent source of energy providing energy to transport at least part of the fluid through the separation unit. Sources are conveniently force gradients, such as pressure gradients, temperature gradients, electrical or chemical potential gradients. Those gradients can be provided by pumps, particularly micropumps, electrical generators, heat reservoirs etc.

The detector unit 16 is either a single detector or an array of detectors, either of the same type or a combination of different detectors. Suitable detectors are based on the emission or absorption of electromagnetic waves (UV-Vis, IR, Flourescence, Raman, NMR) or acoustic waves, or on electrochemical reactions (conductivity/resistance, potentiometric, amperometric) or other conventional detectors as used for example in the field of chromatography (FID, ECD). The detector itself is coupled to a control and data acquisition system (not shown), which could be installed either locally, i.e., in vicinity of the sensor, or remotely, e.g. at the surface.

A more detailed illustration of the example is shown in FIG. 2.

Figure 2A:
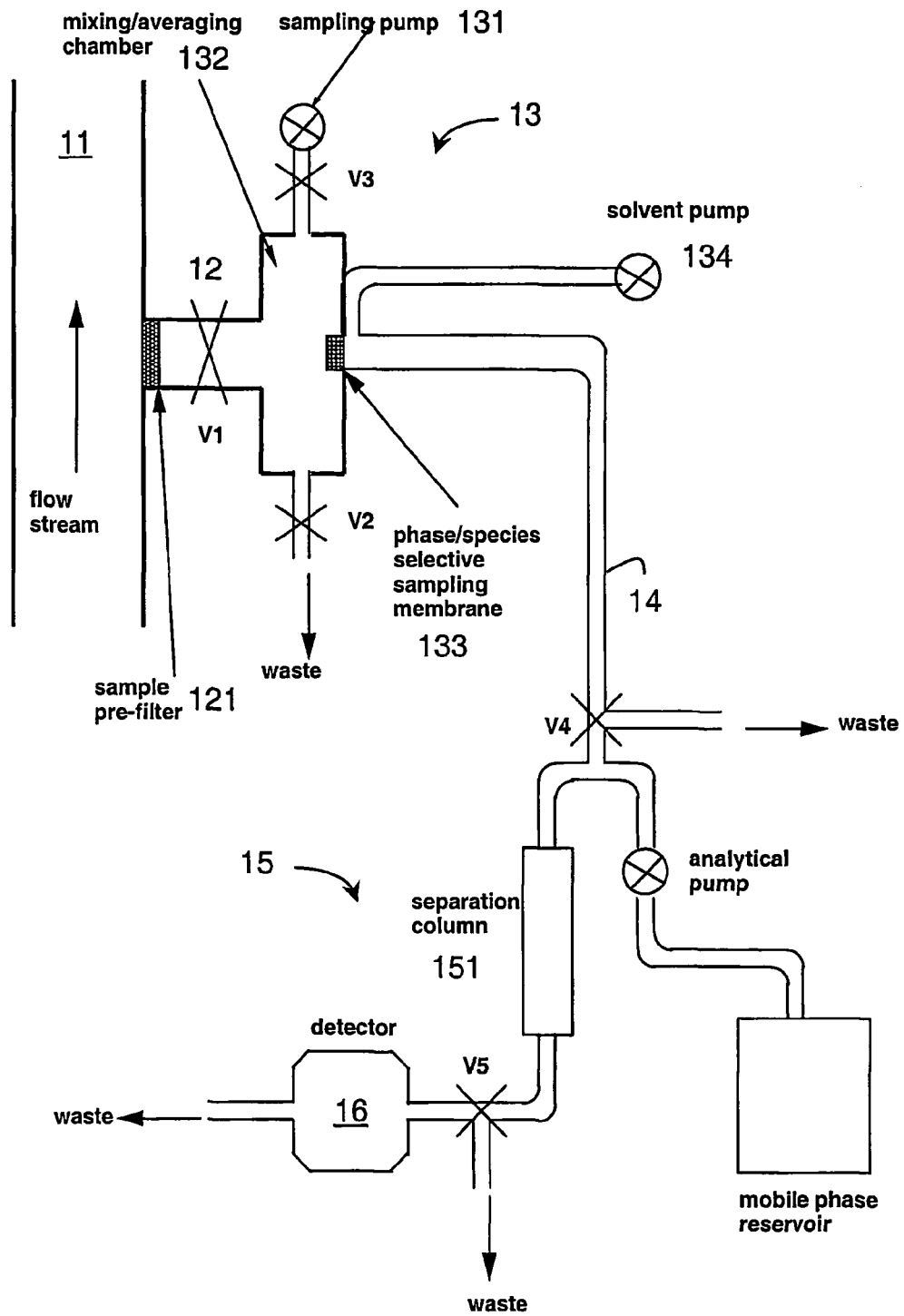

FIG. 2A shows a chemical sensor and attached sampling interface for a multiphase, multicomponent fluid stream. The flow stream is sampled using the sampling interface, which consists of a pre-filter 121 to remove particulate matter, a pump 131 and a chamber 132 to average the composition of the fluid stream over the time between analyses. The fluid from the sample stream is drawn into the sampling chamber through valve V1 using a pump 131. The pump 131 can be used to mix the fluid by pumping it forwards and backwards in the sample chamber 132. The pump is also able to empty the chamber of the sample by pumping to waste or replacing the sample fluid with a second fluid from a reservoir, e.g., for the purposes of calibrating the chemical sensor or cleaning the chamber and associated pipe work. The two inlet ports to the sample chamber are controlled by the use of valves V1 and V2.

When a suitable sample has been captured and mixed in the sample chamber 132 valve V2 is closed and the three-way valve V4 is set to pump the fluid sample to waste. The fluid sample is passed through a membrane filter 133 designed to let pass through a pre-determined phase of the fluid.

The separated phase is pumped to the chemical analysis system using the sampling/mixing pump 131 while the extracted component is pumped to the analytical system using a second pump 134 and a suitable solvent for the extracted phase. For example, in the case of extracted carbon dioxide, the solvent could be a dilute solution of sodium hydroxide; the carbon dioxide is solubilised in the alkaline solution and converted to carbonate (or bicarbonate) ions. The flow rate of solvent is controlled by the second pump 134 and is selected to with knowledge of the known rate of diffusion of the component across the separation membrane 133.

When the sample or component for analysis has been pumped to valve V4 it is switched from waste to the analysis system and an accurately known volume is delivered to the flow line 14 of the analysis system. The volume dose can be controlled either by the delivery pump 134 or using a suitable sample injection system.

The injected sample is pumped through the separation system 15, such as a chromatography column or electrophoresis capillary column 151, and the separated components analyzed by a suitable detector, e.g., electrochemical (potentiometric, amperometric) or optical (spectrophotometric or fluorescent) detectors. Valve V5 can be used to divert certain separated components from the detector to avoid problems of contamination or detector overload.

In the device shown in FIG. 2B, the separator and detector units are merged into one micro-measurement system as is described in more detail below. The separator unit 15 comprises a ion-selective membrane.

Ion-selective membrane electrodes are electrochemical electrodes that can be used in the direct measurement of the activity, and hence concentration, of analyte ions in sample solutions, particularly complex organic solutions. Selectivity for one species over another is determined by the nature and chemical composition of the ion-selective membrane and the associated reaction layers used to fabricate the electrode. Such ion-selective membranes serve as an additional component of a classic two-electrode galvanic cell, with the potential developed at the interface between the membrane and the sample solution being directly or indirectly related to the activity of the analyte ions in the sample solution.

The measurement principle of electrochemical cells incorporating ion-selective membrane electrodes is quite simple. Two electrodes are separated by an ion-selective membrane, with the solution on one side of the membrane being an internal reference solution of known composition and including ions to which one electrode, referred to as the internal electrode, and the membrane respond, and the solution on the other side of the membrane being a sample solution in contact with the other electrode, referred to as the external reference electrode.

In such electrochemical cells the phase-boundary potentials will be constant except for the membrane potential which is the difference in the electrical potential between the internal reference solution and the sample solution; the variation in this membrane potential being an indication of the activity of the analyte ions in the sample solution. In practice, the internal electrode, the internal reference solution and the ion-selective membrane are often housed in a single unit to provide an ion-selective electrode. In this arrangement the voltage is measured as an electromotive force (EMF) between the ion-selective electrode (ISE) and the reference electrode (RE) according to the formula $EMF=E_{ISE}-E_{RE}$.

The measurement system can be a microfabricated potentiometric sensor as disclosed for example in a paper by Uhlig et al entitled "Miniaturized Ion-Selective Chip Electrode for Sensor Applications" as published in Analytical Chemistry, Vol. 69, No. 19, pages 4032 to 4038. These miniaturized sensors are fabricated by depositing a polymeric ion-selective membrane into anisotropically etched wells in a silicon wafer, and, in use, a sample solution is brought into contact with one side of the silicon wafer.

An improved and more rugged version of such a system which includes a separation stage and detection on one chip is described in FIG. 3.

In FIG. 3 there is shown the sensor 31 as fabricated in a substrate chip 32.

The chip 32 includes flow channel 33, in this embodiment of linear section, which includes an inlet port 35 and an outlet port 37 through which a sample solution is in use fed. In this embodiment the flow channel 33 is 10 mm in length, 200 µm in width and 20 µm in depth.

The chip 32 further includes a chamber 39 with an ion-selective membrane 311. The chamber 39 comprises a first, main region 313, in this embodiment of flattened U-shaped section, which includes first and second ports 315, 317 and a second, narrow junction region 319 that communicates directly with the flow channel 33 and extends substantially between midpoints of the main region 313 and the flow channel 33. In this embodiment, the main region 13 is 12 mm in length, 200 µm in width and 20 µm in depth, the first and second ports 315, 317 are 800 µm in diameter, and the junction region 319 is 830 µm in length, 20 µm in width and 20 µm in depth.

In this embodiment the chamber 39 is completely filled with ion-selective membrane 311 as shown. In other embodiments only the junction region 319 of the chamber 39 can be filled with the ion-selective membrane 311 or the U-shaped main region 313 of the chamber 39.

In another embodiment the chamber 39 can include an inert, porous supporting material, such as a ceramic, which is provided to support the ion-selective membrane 311 and improve the mechanical stability thereof.

The chip 32 is fabricated from two plates, in this embodiment composed of microsheet glass. In an alternative embodiment the plates could be formed of silicon wafers. In a first step, one of the plates is etched by HF wet etching to form wells which define the flow channel 33 and the main and junction regions 313, 319 of the chamber 39, with the wells having the respective dimensions mentioned hereinabove. In a second step, four holes are drilled, in this embodiment by ultrasonic abrasion, into the other plate so as to provide the inlet and outlet ports 35, 37 of the flow channel 33 and the first and second ports 315, 317 of the chamber 39. In a third step, the two plates are bonded together by direct fusion bonding. In a fourth step, the junction region 319 of chamber 39 is filled with an organic cocktail that provides the ion-selective membrane 311. Filling is achieved by maintaining a gas flow, typically of an inert gas such as argon, through the flow channel 33 and introducing a predetermined volume of the organic cocktail into one of the ports 315, 317 of the chamber 39. In this way, the main and junction regions 313, 319 of the chamber 39 are filled with the organic cocktail; organic cocktail being prevented from entering the flow channel 33 by the gas flow maintained therethrough. Where the chamber 39 is to include an inert, porous supporting material, this material is introduced prior to or after fusing together the two plates. In a fifth and final step, the chip 32 is allowed to stand until the solvent in the organic cocktail of the ion-selective membrane 311 has evaporated and a dry ion-selective membrane 311 is formed. Typically, the chip 32 is dried in a desiccator.

In this embodiment the organic cocktail comprises tetrahydrofuran (THF) as a solvent, o-nitrophenyloctyl ether (o-NOPE) as a solvent mediator, polyvinyl chloride (PVC) as a polymeric matrix material, potassium tetrakis(4-chlorophenyl)borate (TPB) as a lipophilic salt for reducing electrical resistance, and an ion-transfer agent. Other suitable polymeric matrix materials include fluorosilicone elastomers that have a relatively low resistance and high dielectric constant.

In a preferred embodiment the chamber 39 can be surface treated so as to be of increased hydrophobicity. Preferably, the chamber 39 is silanized by treating with a silane solution. Appropriate silane solutions include the siloxane based solution Repelcote™ and 5% dimethylchlorosilane in carbon tetrachloride. In practice, the chamber 39 is treated after bonding together the two plates by feeding a metered volume of silane solution, typically using a syringe needle, into one of the ports 315, 317 of the chamber 39 and simultaneously applying a vacuum, typically using a vacuum pump, to the other of the ports 315, 317 of the chamber 39 so as to fill the same. In order to prevent the silane solution entering the flow channel 33, a gas flow, typically an inert gas such as argon, is maintained in the flow channel 33. The silane solution is maintained in the chamber 39 for a short time, typically from 2 to 3 minutes, and then completely withdrawn using the vacuum pump. This process is then repeated so as to ensure complete silanization of the chamber 39.

The sensor 31 further comprises a first tubular section 321, one of the ends of which is enlarged and bonded to the chip 32, in this embodiment by an epoxy resin, so as to overlie the first port 315 of the chamber 39; the first tubular section 321 defining a reservoir which contains an internal reference solution, in this embodiment 0.1 M of KCl.

The sensor 1 further comprises an electrode element 325, in this embodiment an Ag/AgCl wire, disposed in the reference solution contained by the first tubular section 321.

The sensor 31 further comprises a second tubular section 327, one of the ends of which is enlarged and bonded to the chip 32, in this embodiment by an epoxy resin, so as to overlie the outlet port 37 of the flow channel 33; the second tubular section 327 defining a reservoir for containing the sample solution fed through the flow channel 33.

The sensor 1 further comprises a reference electrode 329 disposed in the second tubular section 327 so as to contact the sample solution when contained therein. In this embodiment the reference electrode 329 comprises a Flexref™ minaturized Ag/AgCl electrode as available from World Precision Instruments of Stevenage, UK.

The sensor 1 further comprises a third tubular section 331, in this embodiment a fused silica capillary tube, bonded to the chip 32, in this embodiment by an epoxy resin, so as to overlie the inlet port 35 of the flow channel 33.

With this configuration, the ion-selective membrane 311, the reference solution and the electrode element 325 together define an ion-selective electrode, such that, on feeding a sample solution through the flow channel 33, a potential is developed across the ion-selective electrode and the reference electrode 329 corresponding to the membrane potential which is the electrical potential between the reference solution and the sample solution and is representative of the activity of the analyte ions in the sample solution.

Figure 2B:
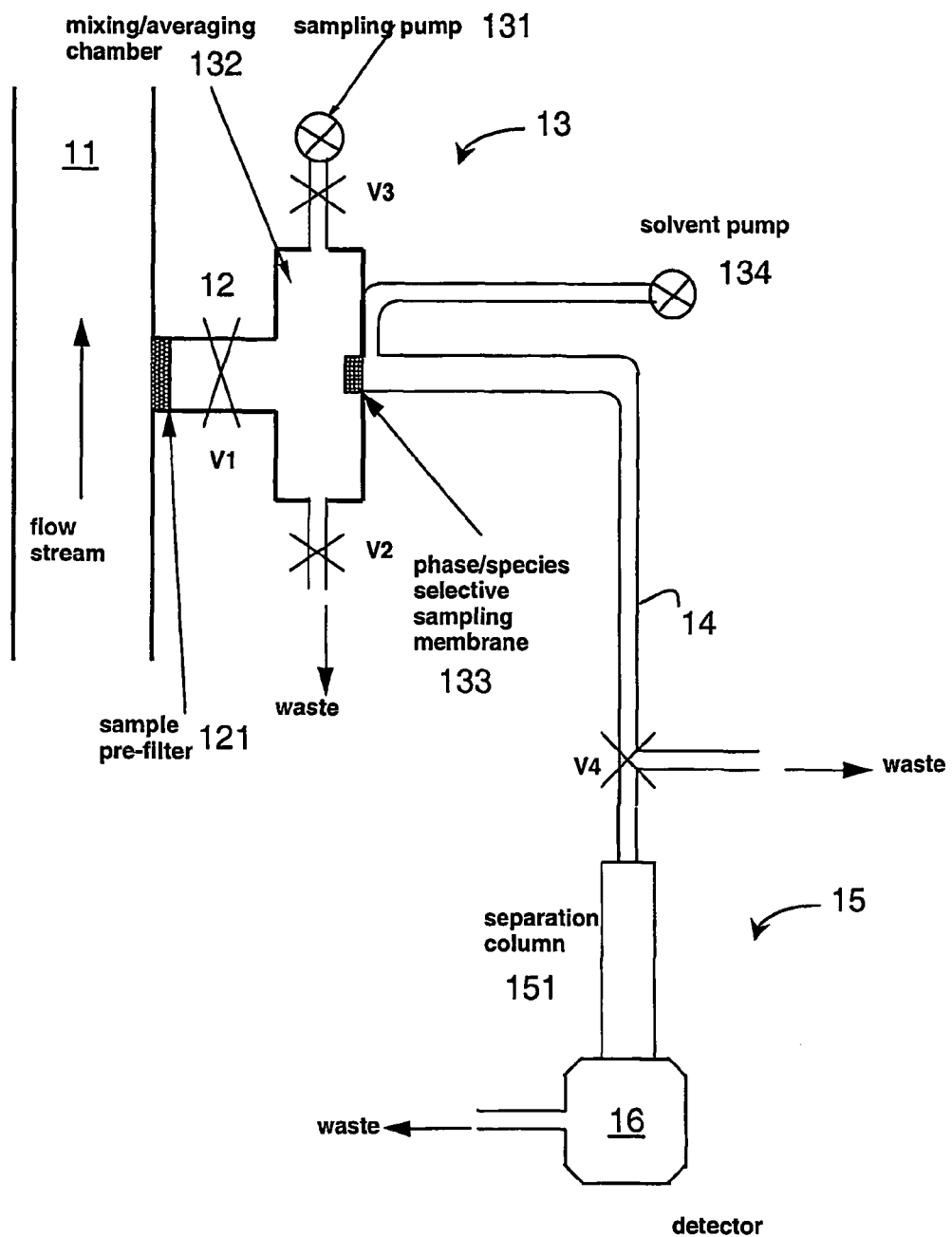

The measurement system further comprises a solution feeder 14, which connects to the first separation unit as shown in FIG. 2B. The measurement system further comprises a data acquisition unit 349 for logging the electromotive force developed across the ion-selective electrode and the reference electrode 329 of the sensor 31. In this embodiment the data acquisition unit 349 comprises a PICO-LOG™ data acquisition system as available from Pico-Technology of Cambridge, UK connected to the ion-selective electrode and the reference electrode 329 through a buffer amplifier for converting the high impedance voltage to a low impedance voltage.

In use, the solution feeder 14 configured to feed a sample solution at a predetermined flow rate through the flow channel 33 of the sensor 31. As this sample solution is fed through the flow channel 33 the electromotive force generated across the ion-selective electrode and the reference electrode 329 is logged by the data acquisition unit 349, which data can be used to provide an on-line measurement of the activity of the analyte ions in the sample solution.

The system further comprises a pump 345 connected by tubing 347 to the sample solution reservoir defined by the second tubular section 327 for feeding the measured solution to waste.

Figure 3A:
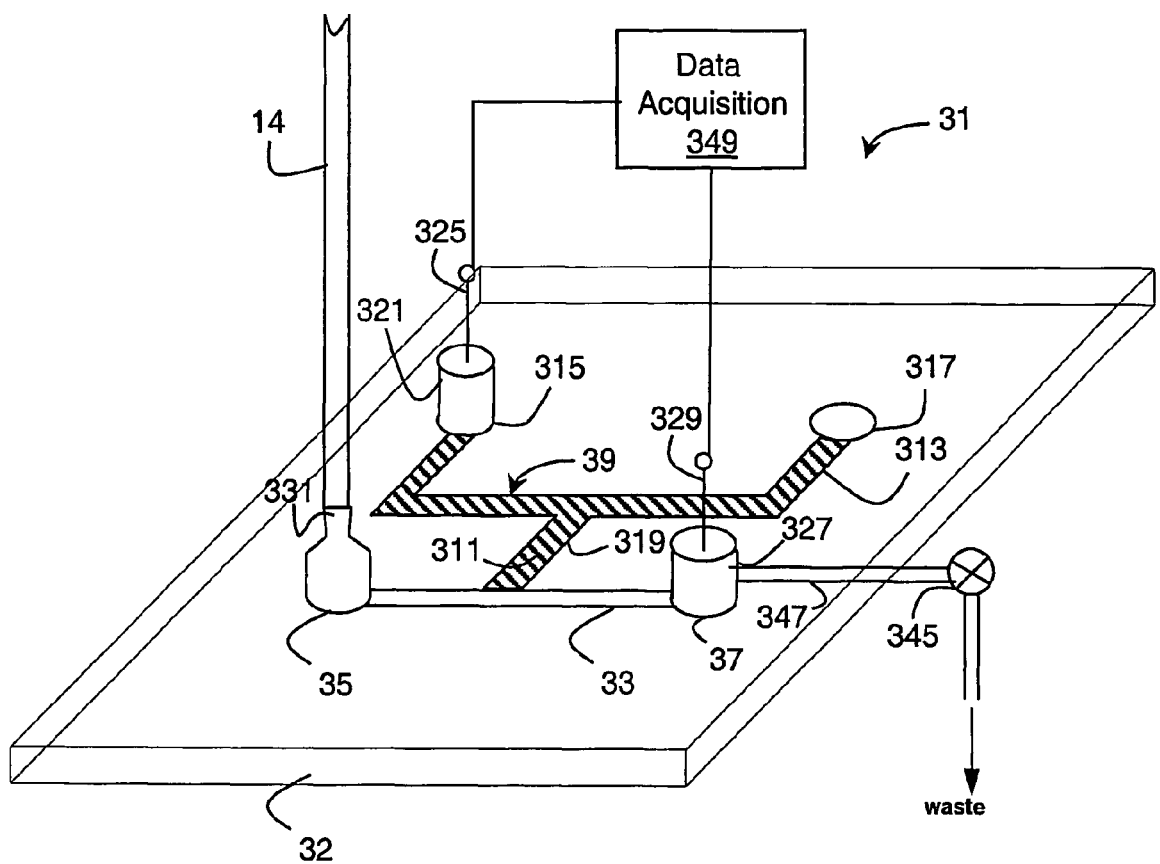
FIG. 3A shows details of a potentiometric sensor with an ion-selective membrane as separator as employed in the example of FIG. 2B.

The example of FIG. 3A can be combined with a further separation method, preferably mounted onto the same substrate.

Figure 3B:
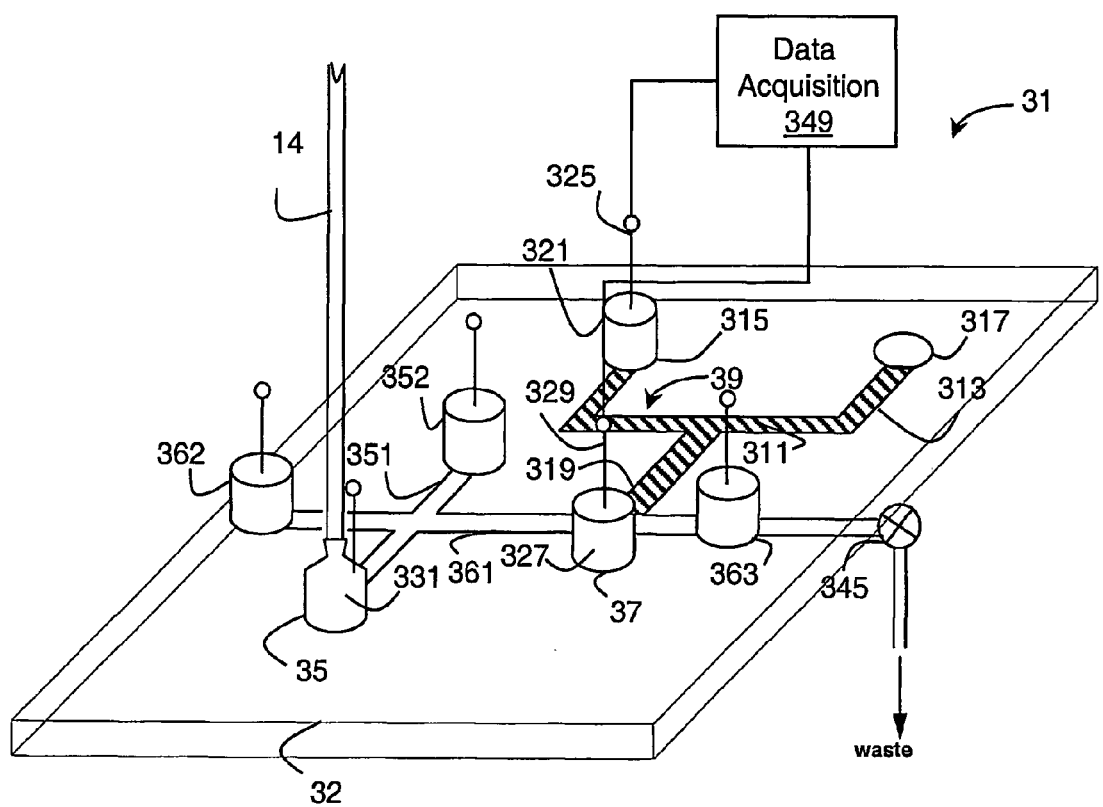
FIG. 3B shows the sensor of FIG. 3A with an additional electrophoretic separation channel.

In FIG. 3B such a further separation stage is shown added to the ion selective sensor of FIG. 3A. Essentially, the separation stage comprises a capillary electrophoretic channel. With an appropriate voltage applied to the buffer fluid reservoirs 362, 363, a sample migrates through the basic electrophoretic channel 361. To load samples into the electrophoretic channel 361, the system operates a cross-flow mechanism. As in the previous example, the initial sample flow is fed via feeder 14 and tube 331 to the inlet port 35. From the inlet port the sample flow is guided through channel 351 to a waste outlet 352. By reducing the voltage across inlet 35 and outlet 352 below the voltage applied to the buffer fluid reservoirs 362, 363, a sample "plug" located at the crossing between the two channels 351, 361 flows along the capillary electrophoretic separation channel 361. In the electrophoretic separation channel 361, the sample is separated according the mobility of its components. Near the end of channel 361, an ion-selective sensor 31 (as described in the previous example) provides an additional separation combined with a quantitative measurement of the ionic concentration in the sample. Fractions of the passing sample are absorbed by the ion-selective membrane and cause a change in the potential difference between electrodes 327 and 325. The system control and data acquisition unit 349 monitors the change.

In the following, a tool in accordance with the present invention is depicted in various types of downhole measurements.

Figure 4:
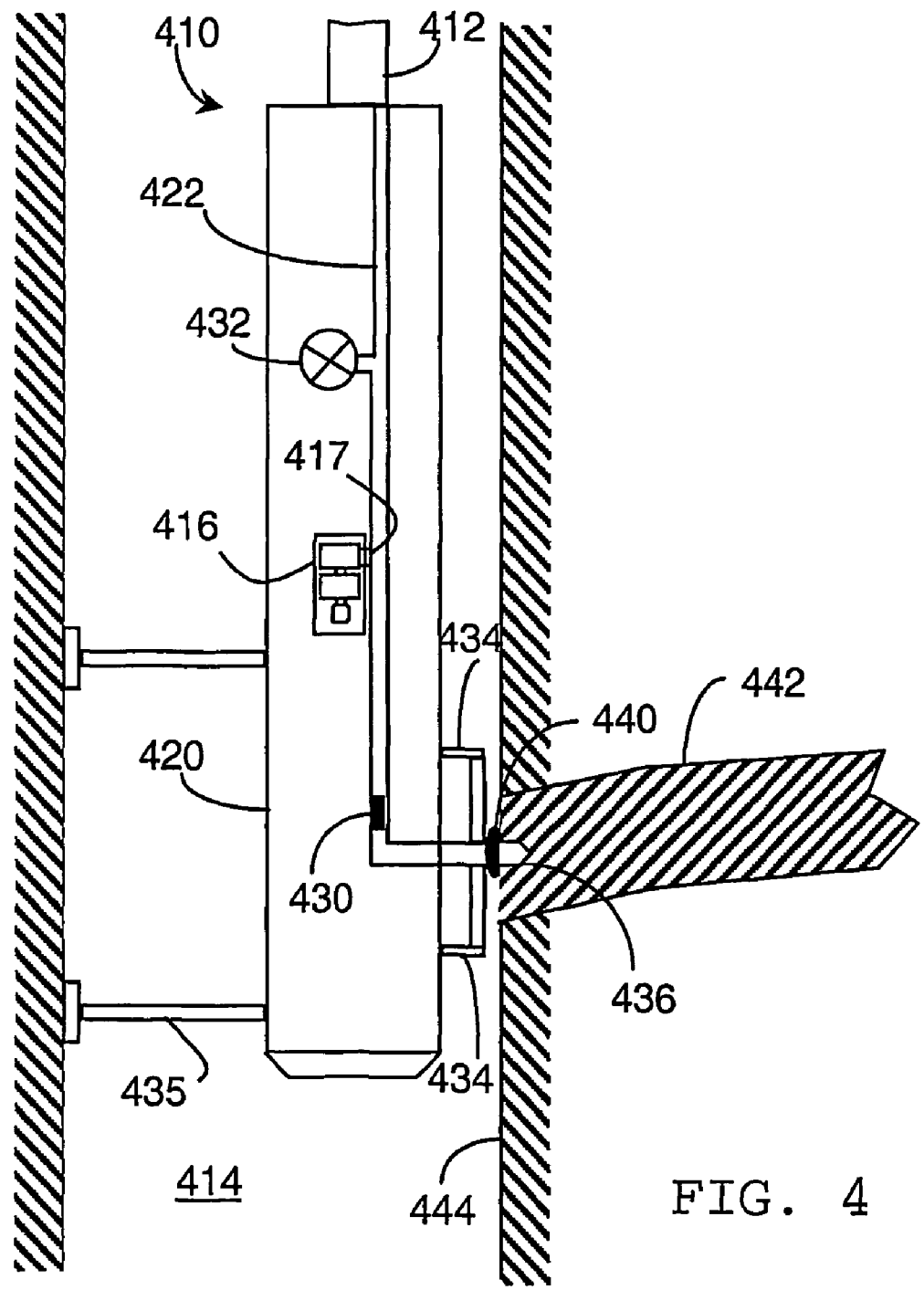
FIG. 4 illustrates the use of the analyzing tool as wireline logging tool.

In FIG. 4, there is shown a formation testing apparatus 410 held on a wireline 412 within a wellbore 414. The apparatus 410 is a well-known modular dynamic tester (MDT, Mark of Schlumberger) as described in the co-owned U.S. Pat. No. 3,859,851 to Urbanosky U.S. Pat. No. 3,780,575 to Urbanosky and U.S. Pat. No. 4,994,671 to Safinya et al., with this known tester being modified by introduction of an analyzing tool 416 as described in detail above. The modular dynamics tester comprises body 420 approximately 30 m long and containing a main flowline bus or conduit 422. The analysing tool 416 communicates with the flowline 422 via opening 417. In addition to the novel sensor system 416, the testing apparatus comprises an optical fluid analyser 430 within the lower part of the flowline 422. The flow through the flowline 422 is driven by means of a pump 432 located towards the upper end of the flowline 422. Hydraulic arms 434 and counterarms 435 are attached external to the body 420 and carry a sample probe tip 436 for sampling fluid. The base of the probing tip 436 is isolated from the wellbore 414 by an o-ring 440, or other sealing devices (packers).

Before completion of a well, the modular-dynamics tester is lowered into the well on the wireline 412. After reaching a target depth, i.e., the layer of the formation which is to be sampled (here: 442), the hydraulic arms 434 are extended to engage the sample probe tip 436 with the formation. The o-ring 440 at the base of the sample probe 436 forms a seal between the side of the wellbore 444 and the formation 442 into which the probe 436 is inserted and prevents the sample probe 436 from acquiring fluid directly from the borehole 414.

Once the sample probe 436 is inserted into the formation 442, an electrical signal is passed down the wireline 412 from the surface so as to start the pump 432 and the sensor systems 416 and 430 to begin sampling of a sample of fluid from the formation 442. The first separation unit of the analyzing system 416 is provided with a silicon rubber membrane. The following electrokinetic separation in the ion-selective channel and the potentiometric detector are adapted to measure the metal ion ($Me^{2+}$) content of the formation effluent.

A further possible application of the novel sensor and separation system is in the field of measurement-while-drilling (MWD). The principle of MWD measurements is known and disclosed in a vast amount of literature, including for example U.S. Pat. No. 5,445,228, entitled "Method and apparatus for formation sampling during the drilling of a hydrocarbon well".

Figure 5:
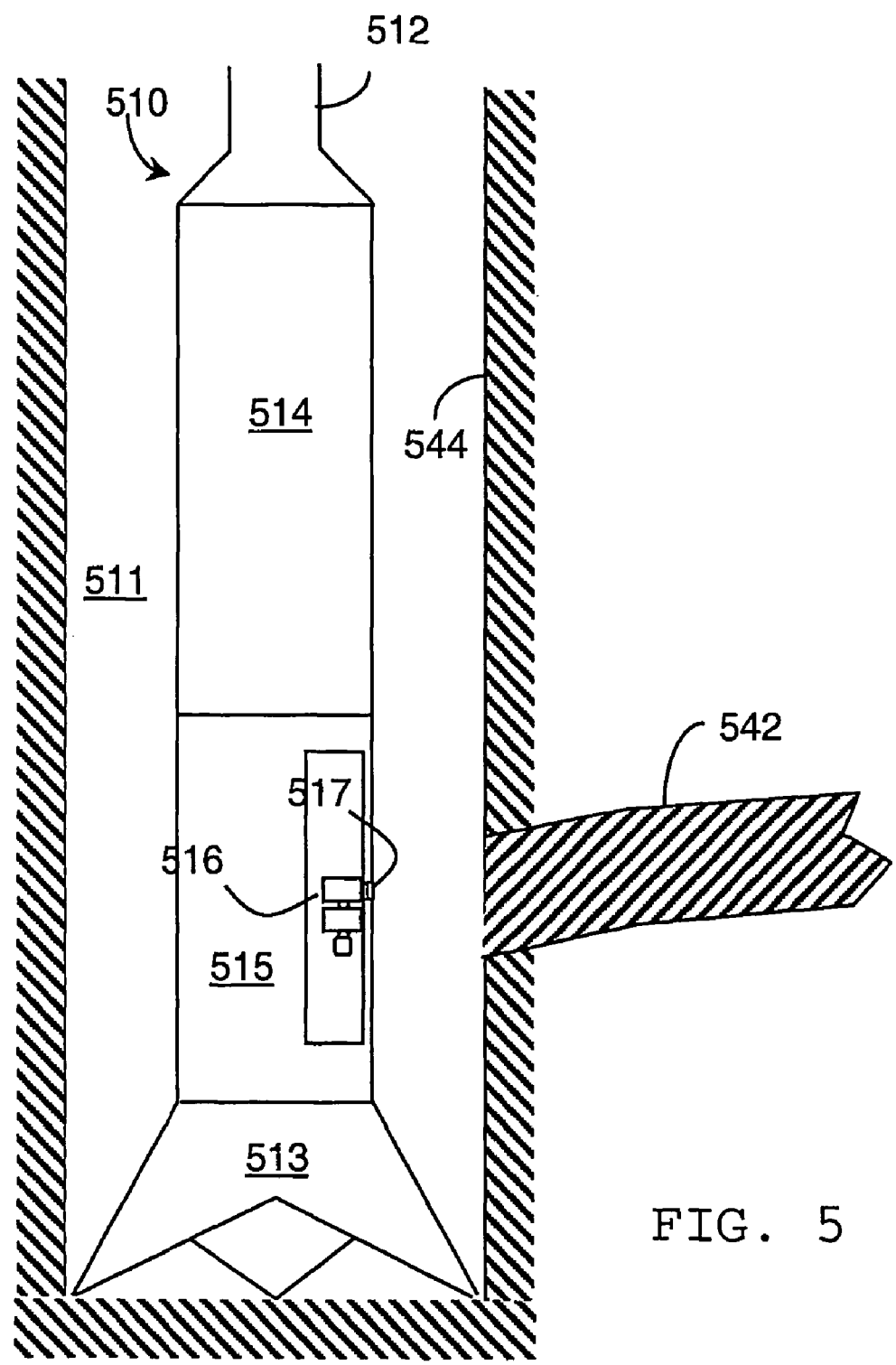
FIG. 5 illustrates the use of the analyzing tool as part of an MWD (measurement-while-drilling) tool.

In FIG. 5, there is shown a wellbore 511 and the lower part of a drill string 512 including the bottom-hole-assembly (BHA) 510. The BHA carries at its apex the drill bit 513. It includes further drill collars that are used to mount additional equipment such as a telemetry sub 514 and a sensor sub 515. The telemetry sub provides a telemetry link to the surface, for example via mud-pulse telemetry. The sensor sub includes the novel analyzing unit 516 as described above. The analyzing unit 516 collects fluids from the wellbore via a small recess 517 protected from debris and other particles by a metal mesh.

During drilling operation wellbore fluid enters the recess 517 and, hence, the first separation unit of the analyzing tool 516. After further separation and detection as described above (FIGS. 2 and 3), the results are transmitted from the data acquisition unit to the telemetry unit 514, converted into telemetry signals and transmitted to the surface.

Figure 6:
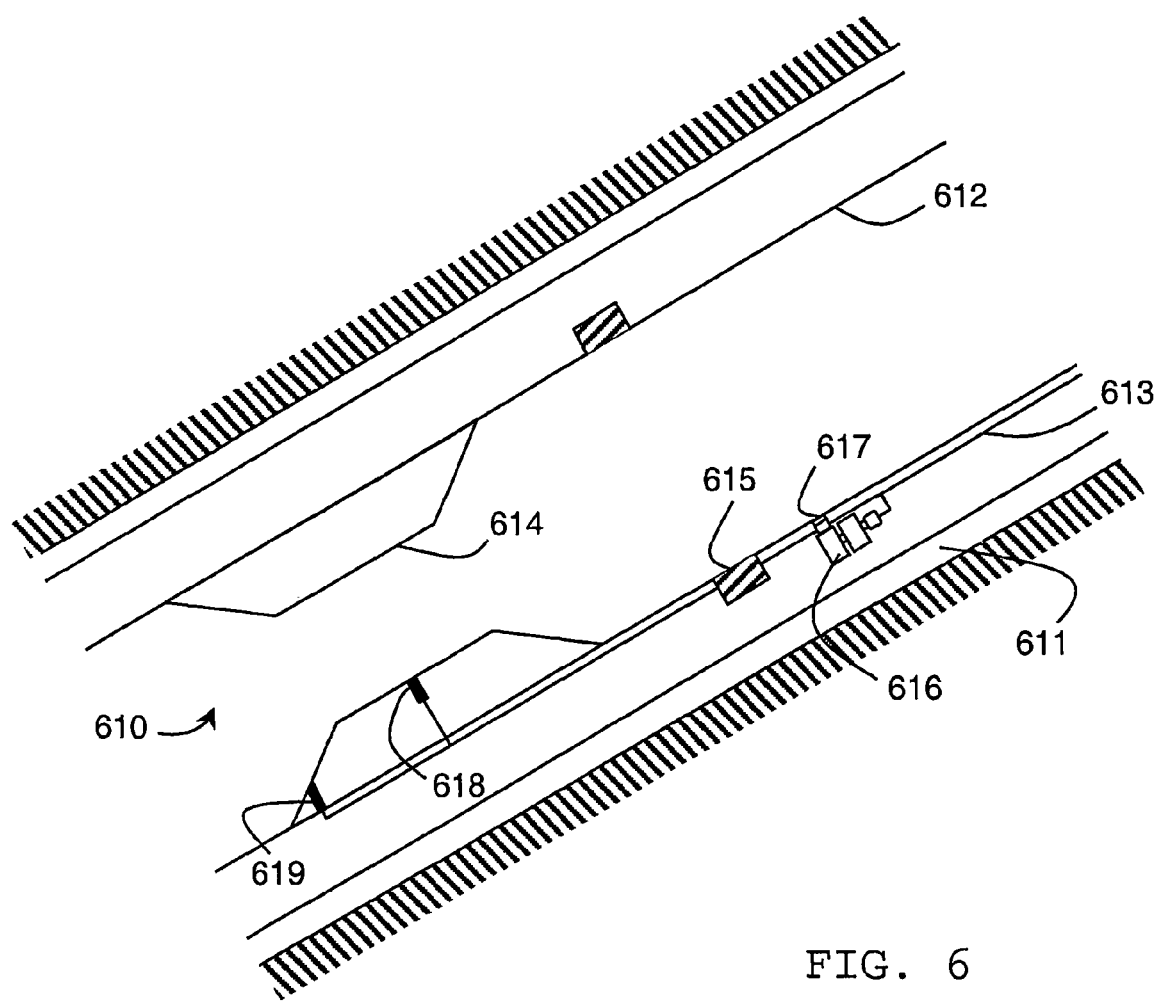
FIG. 6 illustrates the use of the analyzing tool as part of a permanently installed flow monitoring unit in a wellbore.

A third application is illustrated in FIG. 6. It shows a venturi-type flowmeter 610, as well known in the industry and described for example in the U.S. Pat. No. 5,736,650. Mounted on production tubing or casing 612, the flowmeter is installed at a location within the well 611 with a wired connection 613 to the surface following known procedures as disclosed for example in the U.S. Pat. No. 5,829,520.

The flowmeter consists essentially of a constriction or throat 614 and two pressure taps 618, 619 located conventionally at the entrance and the position of maximum constriction, respectively. Usually the venturi is combined with a densiometer 615 located further up- or downstream.

The novel analyzing unit 616 is preferably located downstream from the venturi to take advantage of the mixing effect the venturi has on the flow. A recess 617 protected by a metal mesh provides an inlet to the unit.

During production wellbore fluid enters the recess 617 and, hence, the first separation unit of the analyzing tool 616.

After further separation and detection as described above (FIGS. 2 and 3), the results are transmitted from the data acquisition unit to the surface via the wires 613.

Figure 7:
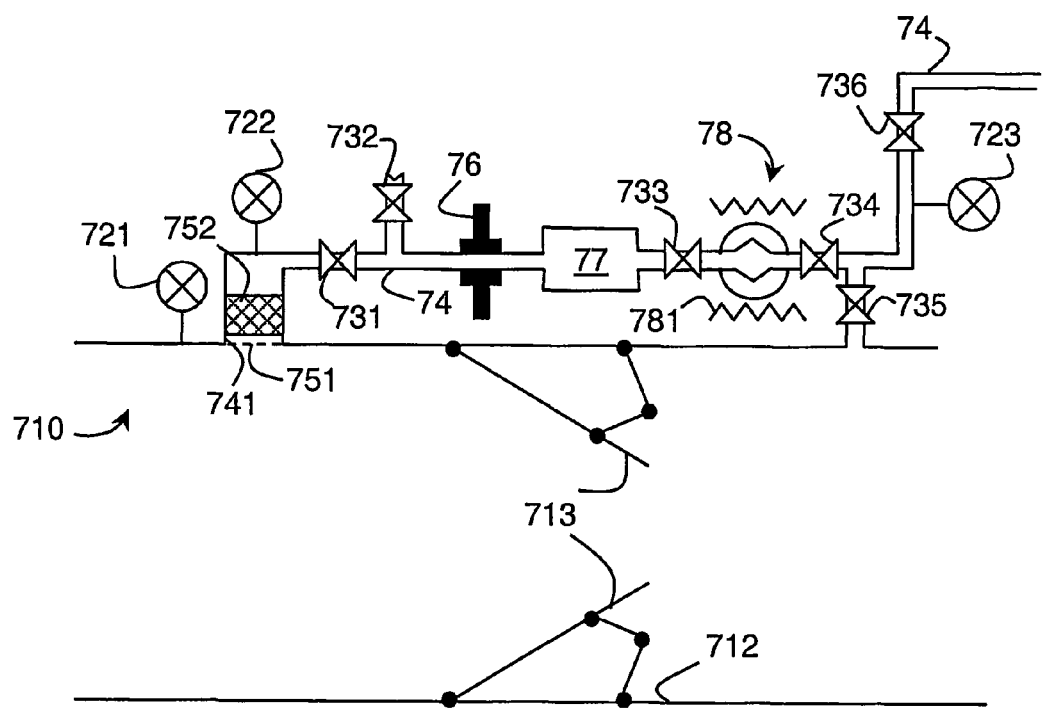
FIG. 7 illustrates a further variant of an analyzing tool as part of a permanently installed flow monitoring unit in a wellbore.

A further example of the present invention is shown in FIG. 7. The illustrated device is part of a downhole installation 710 employed to monitor the flow through a downhole conduit 712. The device by-passes a flow restriction a The monitoring system comprises three pressure sensors 721, 722, 723 and six valves 731–736 located at various position along a conduit 74. The conduit has a first opening 741 covered by a mesh 751. The mesh 751 protects a subsequent phase filter 752. Also positioned along the conduit 74 are a conductivity detector 76 and a mixing chamber 77 followed by a pumping system 78. The pumping system 78 is operated through thermal expansion. The necessary thermal energy is provided by an electrical heating coil 781. The output flowline leads to the on-chip separation and analyzing unit described in FIG. 3.

In operation a multiphase flow 711 is produced from the well and pumped through the conduit 712. A sample from the main conduit is collected through the phase filter 752 (a water saturated ceramic with pore sizes below 1 micron) that allows only the aqueous phase to pass. The fluid sample passes through the filter under a pressure gradient temporarily generated by closing the flow restricting system 713. The pressure gradient can be measured using the pressure transducers 721, 722. When the valve 731 is opened the water sample passes through a conductivity detector 76. The conductivity detector is employed to determine the salinity of the water. Valve 732 is used to release unwanted samples. For further treatment, the sample is collected in the mixing chamber 77 where one or more samples can be mixed to give an averaged representative sample of the fluid over a collection interval. A small pumping system, e.g. a thermal expansion pump, is used to feed a controlled flow into the sensor system for quantitative analysis as described above (FIG. 3). The flow is controlled using valve 736 and the pressure sensor 723. In preparation for further sampling, the conduit 74 can be flushed via valve 735.

The above examples illustrate possible uses of the novel analyzing tool, but are not meant to exclude other possible application of the analyzing tool in the field of wellbore fluid analysis.

The invention claimed is:

1. A wellbore effluent analyzing device for downhole analysis of the wellbore effluent, comprising:
   a main conduit carrying in operation said wellbore effluent;
   a sample channel communicating through at least one opening with said main conduit;
   a first phase separation stage, wherein said first phase separation stage is configured to generate a forced flow of a sample of said wellbore effluent through a first phase separation member, and wherein said first phase separation member is configured to allow a pre-determined phase of said flowing sample to pass through said first phase separation member;
   a second separation stage configured to generate a forced flow of at least part of said pre-determined phase through a second separation member to provide a further separated sample, wherein said second separation member is configured to separate the at least part of said pre-determined phase according to chemical or physical properties; and
   a sensor unit to detect components of said further separated sample.

2. An analyzing device according to claim 1 wherein the second separation stage comprises a migration path or column filled with material providing different migration velocities to different molecules.

3. An analyzing device according to claim 1 wherein at least one of the first phase separation stage and the second separation stage comprises a membrane as separation member.

4. An analyzing device according to claim 3 wherein the membrane is made of material selected from a group comprising PTFE, $ZrSO_4$, or silicon rubber.

5. An analyzing device according to claim 3 wherein the membrane is ion-selective.

6. An analyzing device according to claim 1 comprising a pumping system generating a forced flow through at least one of the first phase separation member and the second separation member.

7. An analyzing device according to claim 1 comprising an electrical voltage generator to generate a forced flow through at least one of the first phase separation member and the second separation member.

8. An analyzing device according to claim 1 wherein at least one of the separation stages and the sensor unit are microfabricated.

9. An analyzing device according to claim 1 wherein at least one of the separation stages and the sensor unit are mounted on a common substrate.

10. An analyzing device according to claim 1 wherein the sensor unit is sensitive to charged atoms or molecules.

11. An analyzing device according to claim 1 wherein the sensor unit is sensitive to organic molecules.

12. An analyzing device according to claim 1 housed in a body adapted to engage with a wireline and to be suspended from said wireline.

13. An analyzing device according to claim 1 housed in a body wherein the body is mounted on a drill string.

14. An analyzing device according to claim 1 wherein the analyzing device is mounted on a production or casing well tubular.

15. An analyzing device according to claim 1 further comprising a solid removal filter or mesh located in flow direction before said first phase separation stage.

16. An analyzing device according to claim 10 wherein the sensor unit is sensitive to charged atoms or molecules selected from a group consisting of $Ca^{2+}$, $Mg^{2+}$, $Sr^{2+}$, $Ba^{2+}$, $Na^+$, $K^+$, $CO_3^{2-}$, $SO_4^{2-}$, $PO_4^{3-}$ and $Cl^-$.

17. An analyzing device according to claim 10 wherein the sensor unit comprises a potentiometric sensor.

* * * * *

UNITED STATES PATENT AND TRADEMARK OFFICE
CERTIFICATE OF CORRECTION

PATENT NO. : 7,231,819 B2
APPLICATION NO. : 10/297773
DATED : June 19, 2007
INVENTOR(S) : Jones et al.

It is certified that error appears in the above-identified patent and that said Letters Patent is hereby corrected as shown below:

Title Page:

Item 30
Under "Foreign Application Priority Data,"
"Aug. 21, 2000   (GB) ……………………………… 0015052.4"
should be replaced with
--June 21, 2000   (GB) …………………………….. 0015052.4--

Signed and Sealed this

Fourteenth Day of August, 2007

JON W. DUDAS
*Director of the United States Patent and Trademark Office*